United States Patent
Sawyer

(10) Patent No.: US 8,055,323 B2
(45) Date of Patent: Nov. 8, 2011

(54) STEREOTACTIC SYSTEM AND METHOD FOR DEFINING A TUMOR TREATMENT REGION

(75) Inventor: Timothy E. Sawyer, Boise, ID (US)

(73) Assignee: ImQuant, Inc., Boise, ID (US)

(*) Notice: Subject to any disclaimer, the term of this patent is extended or adjusted under 35 U.S.C. 154(b) by 2253 days.

(21) Appl. No.: 10/910,483

(22) Filed: Aug. 3, 2004

(65) Prior Publication Data

US 2005/0033108 A1 Feb. 10, 2005

Related U.S. Application Data

(60) Provisional application No. 60/492,796, filed on Aug. 5, 2003, provisional application No. 60/508,117, filed on Oct. 2, 2003, provisional application No. 60/534,633, filed on Jan. 7, 2004.

(51) Int. Cl.
*A61B 5/05* (2006.01)

(52) U.S. Cl. .......................... 600/407; 606/130

(58) Field of Classification Search .................. 600/425, 600/426; 606/130; 378/65
See application file for complete search history.

(56) References Cited

U.S. PATENT DOCUMENTS

| 4,736,307 A | 4/1988 | Salb |
| 5,373,844 A | 12/1994 | Smith et al. |
| 5,418,827 A | 5/1995 | Deasy et al. |
| 5,517,990 A * | 5/1996 | Kalfas et al. .................. 600/414 |
| 5,622,187 A | 4/1997 | Carol |
| 5,661,773 A | 8/1997 | Swerdloff et al. |
| 5,740,802 A | 4/1998 | Nafis et al. |
| 5,859,891 A | 1/1999 | Hibbard |
| 5,868,673 A | 2/1999 | Vesely |
| 5,871,018 A | 2/1999 | Delp et al. |
| 6,067,372 A | 5/2000 | Gur et al. |
| 6,104,779 A | 8/2000 | Shepherd et al. |
| 6,112,112 A | 8/2000 | Gilhuijs et al. |
| 6,167,296 A | 12/2000 | Shahidi |
| 6,222,544 B1 | 4/2001 | Tarr et al. |
| 6,226,352 B1 | 5/2001 | Salb |
| 6,236,875 B1 | 5/2001 | Bucholz et al. |
| 6,239,724 B1 | 5/2001 | Doron et al. |
| 6,258,104 B1 | 7/2001 | Kreizman et al. |
| 6,292,578 B1 | 9/2001 | Kalvin |
| 6,335,980 B1 | 1/2002 | Armato, III et al. |
| 6,347,240 B1 | 2/2002 | Foley et al. |
| 6,398,710 B1 | 6/2002 | Ishikawa et al. |
| 6,405,072 B1 * | 6/2002 | Cosman .......................... 600/426 |
| 6,422,748 B1 | 7/2002 | Shepherd et al. |
| 6,434,415 B1 | 8/2002 | Foley et al. |
| 6,470,207 B1 | 10/2002 | Simon et al. |

(Continued)

FOREIGN PATENT DOCUMENTS

WO 2004033041 A1 4/2004

*Primary Examiner* — Parikha Mehta

(74) *Attorney, Agent, or Firm* — Quarles & Brady LLP

(57) ABSTRACT

An instrument is used to mark locations in tissue that define the boundary of a three-dimensional treatment zone. The position of the instrument is recorded by a tracking system and a treatment zone image is produced which depicts the treatment zone along with patient reference points also marked by the instrument. The treatment zone image is exported to a radiation treatment system which uses the patient reference points to align the treatment zone image with the patient and uses the treatment zone image to aim the radiation.

15 Claims, 6 Drawing Sheets

U.S. PATENT DOCUMENTS

| | | |
|---|---|---|
| 6,546,073 B1 | 4/2003 | Lee |
| 6,556,695 B1 | 4/2003 | Packer et al. |
| 6,669,635 B2 | 12/2003 | Kessman et al. |
| 6,675,810 B2 | 1/2004 | Krag |
| 6,681,129 B2 | 1/2004 | Matsuzaki et al. |
| 6,694,057 B1 | 2/2004 | Miller et al. |
| 2003/0211036 A1 | 11/2003 | Degani et al. |
| 2004/0122311 A1 | 6/2004 | Cosman |
| 2004/0138556 A1 | 7/2004 | Cosman |

* cited by examiner

STEREOTACTIC SYSTEM AND METHOD FOR DEFINING A TUMOR TREATMENT REGION

CROSS-REFERENCE TO RELATED APPLICATIONS

This application claims the benefit of U.S. Provisional patent application Ser. No. 60/492,796 filed on Aug. 5, 2003 and entitled "Method For Generation Of Exportable Three-Dimensional Tumor Volumes From Radiographic Images And Other Digital Systems, And Real-Time Incorporation Of These Volumes Into Biopsy, Endoscopy, Surgery, Radiation Therapy Planning, and Radiation Therapy Delivery Guidance"; U.S. Provisional patent application Ser. No. 60/508,117 filed on Oct. 2, 2003 and entitled "System For The Incorporation Of Intra-Operative Data Into Three-Dimensional Volumes Used As Targets During Surgical Guidance, And For The Mathematical Analysis Of Three-Dimensional Target Volumes," and U.S. Provisional patent application Ser. No. 60/534,633 filed Jan. 7, 2004 and entitled "Software And Hardware Integrating The Isonumeric Volume-Based Imaging Format In An Oncology Patient-Management Workstation, For Rapid Response Assays With Or Without Image Creation, For Software Facilitating Dynamic Chemotherapy Administration, For Image Interpretation And Analysis, And For Advanced Real-Time Image Guidance In Soft Tissue."

BACKGROUND OF THE INVENTION

The field of the invention is the treatment of tumors, and particularly, the identification of a region to be treated with a radiation therapy device or the like.

There are currently three common methods used to communicate key operative findings to a radiation oncologist for use in intra-operative and post-operative radiation therapy. First, the surgeon may describe the operative findings, both by speaking directly with the radiation oncologist, and by dictating his findings in the operative note. With this method, the radiation oncologist makes a best attempt to utilize this information by digitizing the area of concern described by the surgeon on a CT image that has been imported to the radiation therapy planning workstation. Much can be lost in this translation. In addition, it is often considerably more difficult to precisely identify a soft tissue area of concern on a post-operative CT scan than it is to identify it intra-operatively, especially when the person identifying the area of concern intra-operatively (the surgeon) is usually different than the person attempting to identify the same area on the post-operative CT scan (the radiation oncologist).

Second, the surgeon may embed radio-opaque metallic clips into soft tissue surrounding the area of concern, to outline the area of concern. The radiation oncologist then identifies these clips on the simulation film or planning CT images, and adjusts the radiation field shape to ensure that the clips are incorporated in the treatment field. However, interpreting the area of concern (a three-dimensional shape) on a two-dimensional simulation film can cause the radiation oncologist to misinterpret the area of concern. In addition, the clips do not outline the entire border of concern. Rather, three to six "representative" clips are generally placed, spread over the entire border of concern. Finally, it can be difficult to differentiate these clips from clips placed for other purposes at the time of surgery, and the tumor identification clips can be difficult to find on the post-operative planning CT images.

Third, intra-operative irradiation may be delivered by directly visualizing the area of concern, and adjusting the linear accelerator electron cone in an attempt to ensure that the area of concern is contained within the borders of the cone. Poor lighting, blood pooling, the placement of suction devices, the use of bolus material to increase dose at the surface, difficult angles, and visual obstruction caused by the cone can make targeting vague. Clips may be placed by the surgeon to outline the area of concern, but for the reasons described above, these clips can be difficult to visualize as the radiation oncologist sets the electron cone position.

SUMMARY OF THE INVENTION

The present invention is a method and system for accurately communicating a three-dimensional treatment zone for subsequent treatment procedures such as radiation therapy. More specifically, the method includes registering patient location and orientation with a pointer locating system by identifying a plurality of patient reference points using the pointer locating system; identifying and storing a plurality of treatment zone boundary points using the pointer locating system; and producing a three-dimensional treatment zone image from the stored boundary points. The patient reference points may be anatomical landmarks that can easily be located on a CT image or the like by the radiation oncologist, in which case their identity is stored along with their location as part of the treatment zone image information. In the alternative, fiducials may be placed at each patient reference point to make the subsequent registration of the treatment zone image with the treatment system frame of reference easier. In the case of intra-operative radiation therapy delivery, surface markers may also be used for registration.

A general object of the invention is to more accurately convey a surgeon's instructions on the region to be treated following the biopsy or resection of a tumor. Using a surgical instrument that acts as a locating system pointer, the surgeon can identify as many points on the treatment zone boundary as are needed to define the contour of the three-dimensional treatment zone image. These data are used to produce a 3D treatment zone image that may be exported for use in a radiation planning workstation or the like.

Another object of the invention is to enable a radiation therapy system frame of reference to register with the frame of reference of the treatment zone image. This is accomplished by employing fiducials to establish the patient reference points. These fiducials are chosen to be compatible with a patient locating system associated with the radiation therapy system such that registration of the patient and the treatment zone image to the radiation field produced by the treatment system can be made.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
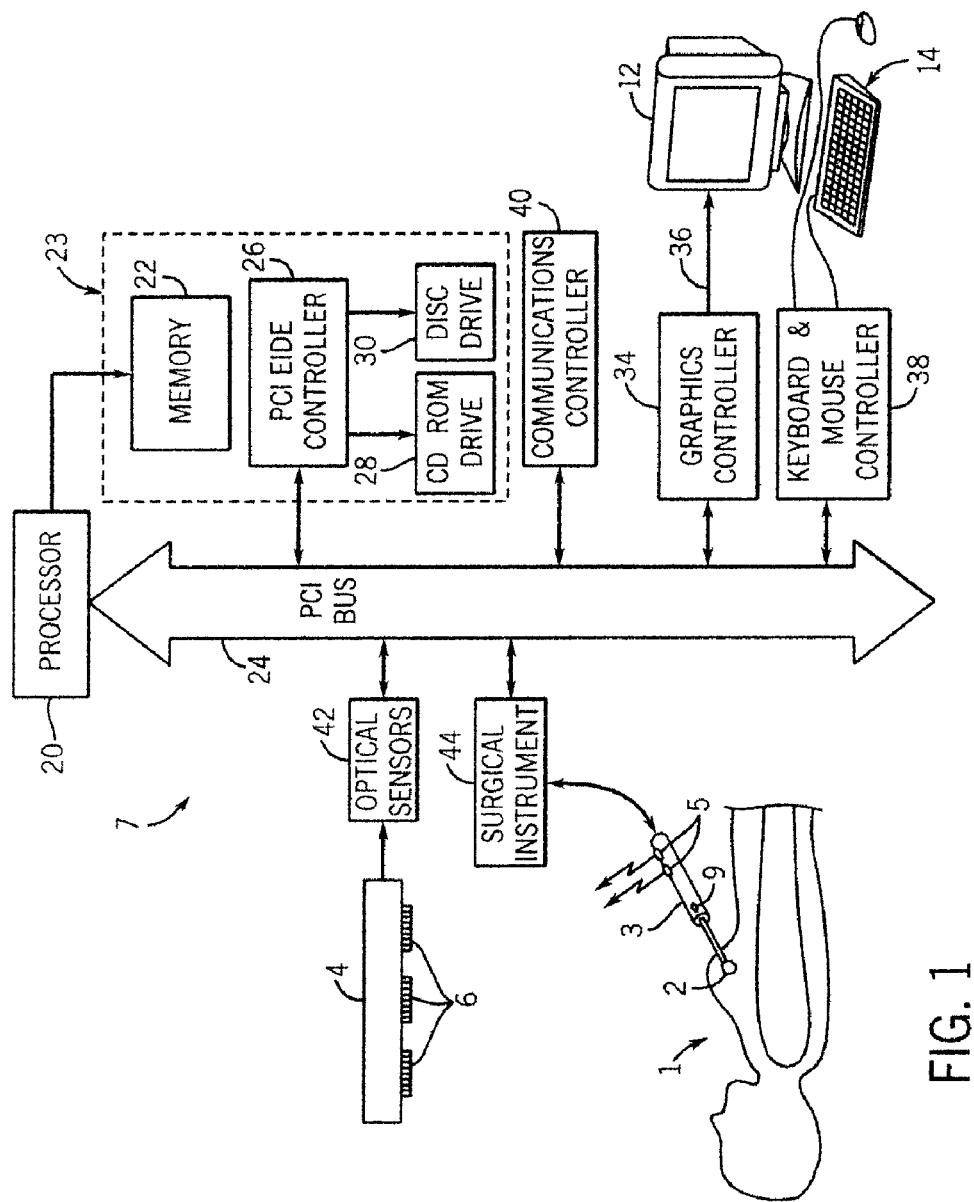
FIG. 1 is a block diagram of a workstation with integral optical tracking system that is programmed to produce three-dimensional treatment zone images according to a preferred embodiment of the invention.

Referring particularly to FIG. 1, a patient 1 having a breast tumor 2 will typically undergo an operation in which the tumor 2 is biopsied or resected. The present invention is a method and system that enables the surgeon to mark the location of the tumor and produce an image of a region to be treated that can be conveyed and used in connection with subsequent radiation therapy. A surgical probe, or instrument 3 is held by the surgeon and used to mark locations in the patient 1. The instrument 3 forms part of an optical tracking system ("OTS") that includes a sensing unit 4 mounted above the patient 1. At least two light emitting diodes 5 mounted on the handle of the surgical instrument 3 emit continuous streams of pulsed infrared signals which are sensed by a plurality of infrared sensors 6 mounted on the sensing unit 4. The instrument 3 and sensing unit 4 are both connected to a computer workstation 7, which controls the timing and synchronization of the pulse emissions from LEDs 5 and the recording and processing of the infrared signals received by detectors 6.

The computer workstation 7 includes a processor 20 which executes program instructions stored in a memory 22 that forms part of a storage system 23. The processor 20 is a commercially available device designed to operate with one of the Microsoft Corporation Windows operating systems. It includes internal memory and I/O control to facilitate system integration and integral memory management circuitry for handling all external memory 22. The processor 20 also includes a PCI bus driver which provides a direct interface with a 32-bit PCI bus 24.

The PCI bus 24 is an industry standard bus that transfers 32-bits of data between the processor 20 and a number of peripheral controller cards. These include a PCI EIDE controller 26 which provides a high-speed transfer of data to and from a CD ROM drive 28 and a disc drive 30. A graphics controller 34 couples the PCI bus 24 to a CRT monitor 12 through a standard VGA connection 36, and a keyboard and mouse controller 38 receives data that is manually input through a keyboard and mouse 14.

The PCI bus 24 also connects to a communications controller 40. The controller 40 connects to an intranet that links the workstation 7 to other institution systems such as imaging systems, PAC systems and treatment systems. The sensing unit 4 interfaces with the PCI bus 24 through an optical sensor circuit 42, and the instrument 3 interfaces with the PCI bus 24 through a surgical instrument circuit 44.

An OTS program executed by the processor 20 operates the surgical instrument 3 and sensing unit 4 to generate data indicating the location and orientation of the tip of the instrument 3 with respect to its coordinate system. This instrument position data is produced on a real time continuous basis, so that as the surgical instrument 3 is moved, its position and orientation are continually tracked and recorded by the sensing unit 4. Position and orientation data are produced whenever a push button switch 9 on the instrument 3 is depressed. The OTS is preferably of the type known as the "Flash Point 3-D Optical Localizer", which is commercially available from Image Guided Technologies of Boulder, Colo. and similar to the systems described in U.S. Pat. Nos. 5,627,857 and 5,622,170. The invention is not limited, however, to the particular type of tracking system used and other modalities may also be used.

Figure 2:
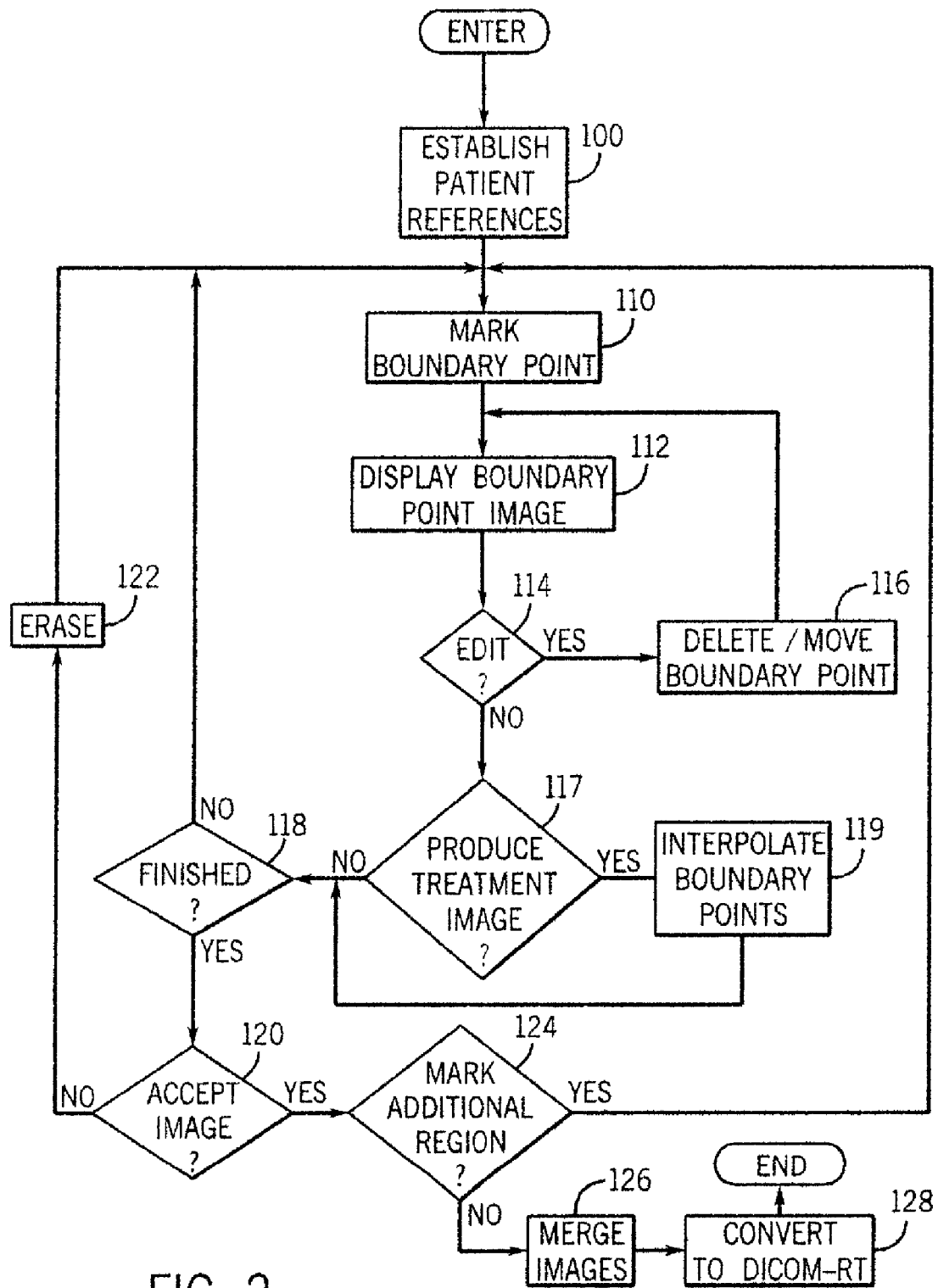
FIG. 2 is a flow chart of the steps performed with the workstation of FIG. 1 to produce a three-dimensional treatment zone image.
Figure 3:
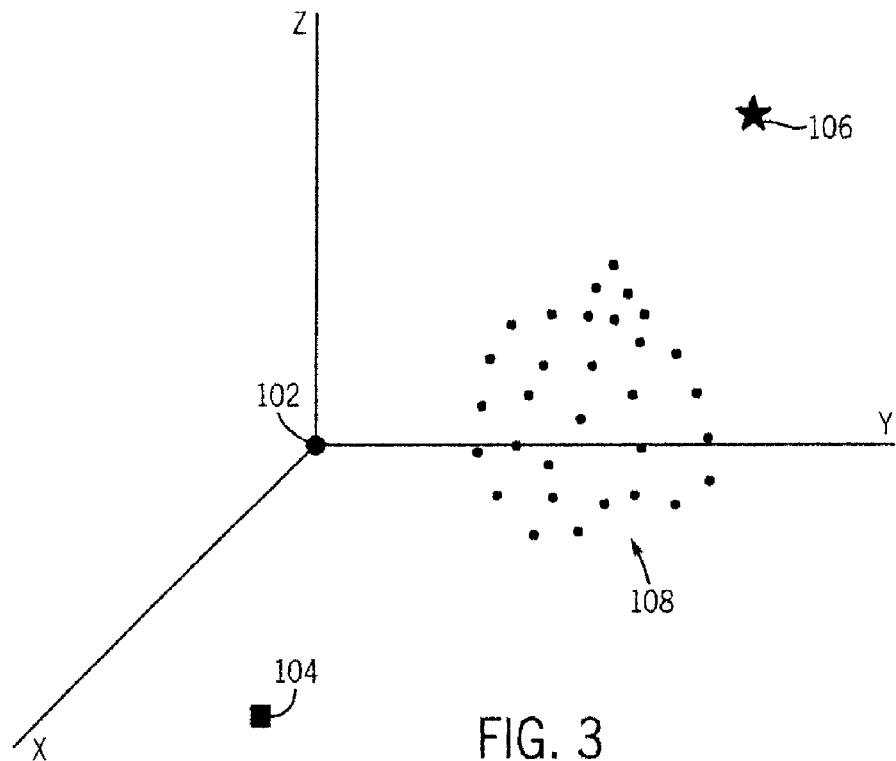
FIG. 3 is a pictorial representation of patient reference points and a boundary point image of an exemplary treatment zone produced with the workstation of FIG. 1.

Referring particularly to FIG. 2, the processor 20 also executes a program which interacts with the surgeon to produce a three-dimensional treatment zone image. As indicated by process block 100, the first step in this process is to establish reference points in the patient using the instrument 3. This step can be performed in two ways. First, the instrument may be moved to easily identifiable, fixed points in the patient. For example, such points might be vascular branch points and small skeletal landmarks that surround a tumor in the pelvis. As the instrument 3 is pointed at each selected patient reference point, the button 9 is depressed to record and store the patient reference point. At the same time the surgeon may record the identity of this anatomic landmark which is stored along with the reference point data. As shown in FIG. 3, the first reference point 102 serves as the origin of the OTS coordinate system and at least two additional patient reference points 104 and 106 surround the region containing the tumor 2 indicated generally at 108. These patient reference points may be indicated on the treatment zone image with different shaped icons so that each patient reference point can be associated with the proper anatomical landmark description.

A second method for establishing the patient reference points is to implant fiducials at locations around the tumor. This method is preferred in clinical situations such as breast cancer where the tumor is surrounded by soft tissues and there are few fixed anatomical landmarks available. The fiducial is implanted using the instrument 3, and when a fiducial is released, the button 9 is depressed to record its position. Alternatively, fiducials may be placed via a simple needle and trochar loading system. With this approach, or if surgical clips are used as fiducials, once the fiducials are placed, their locations are recorded as described above using the tip of the instrument 3. There are many types of fiducials available and the particular type used will depend primarily on the capabilities of the planning system or treatment system to which the treatment zone image is exported. For example, the fiducials may be opaque to x-rays if the treatment system employs a CT image to register its coordinate system with the patient. Or, the fiducials may reflect ultrasound if an ultrasound image is used for treatment system registration. Or, a radio frequency positioning system as described in patent application publication US 2004/0133101 A1 entitled "Guided Radiation Therapy System" may be used in lieu of a medical image to register the treatment system, in which case the fiducials used may be RFID tags that emit radio frequency signals when interrogated.

Referring again to FIG. 2, after the patient reference points have been selected and stored, the three-dimensional contour of the treatment zone is marked using the instrument 3. As indicated by process block 110 the tip of instrument 3 is placed at a location by the surgeon and the button 9 is depressed and released to record and store the position data. These data represent the location of the boundary point as measured from the origin of the OTS coordinate system established by the first patient reference point 102. As indicated at process block 112, an updated image is then output to display 12 that depicts the selected boundary points that have been marked and the surrounding patient reference points 102, 104 and 106. As shown in FIG. 3, this image may show only the boundary points 108 that have been identified so that it can be updated very fast. This enables the surgeon to depress and release the button 9 very rapidly to record boundary points and see their three-dimensional disposition evolve. This "boundary point" image may be revolved to view it from any angle.

As indicated by decision block 114 and process block 116, the operator is then given an opportunity to edit the acquired data point. The data point can either be deleted, or it can be manually moved. In either case, the system loops back to update the displayed image at process block 112. It is contemplated that the surgeon will quickly identify the outline of the treatment zone by marking from 6 to 50 points in this manner.

Because the precise boundary of the three-dimensional treatment zone can be difficult to discern from a collection of points projected onto the two-dimensional monitor 12, the surgeon may elect to produce a 3D treatment zone image as indicated at decision block 117. A button (not shown) is depressed to do this, and as indicated at process block 119, a cubic spline interpolation produces a 3D surface which smoothly connects the boundary points. This 3D treatment zone boundary surface can be rotated in space to view it from any desired angle. The maximum diameter of the 3D treatment zone boundary is also automatically calculated and displayed.

If the treatment drawing is completed as determined by the surgeon at decision block 118, the surgeon is given the opportunity to accept or reject the treatment drawing at decision block 120. If the drawing is not complete, the system loops back to mark additional boundary points at process block 110. If the drawing is finished but not accepted, the drawing is erased as indicated at process block 122 and the system loops back to start re-acquiring boundary points for a new image.

After the treatment zone image is completed, the surgeon is given the opportunity at decision block 124 to draw boundaries for additional regions. Such additional regions may be, for example, a region near the treatment zone previously described which contains critical tissues that should not be exposed to significant radiation. The system loops back to acquire the boundary points for the additional region which are stored as a separate image. This can be repeated to produce images for additional regions if needed.

If more than one image has been acquired and produced as described above, they are merged into a single image as indicated at process block 126. Each specified region is interpolated as described above and each resulting 3D contour surface is displayed in a different color to minimize confusion. The final image can then be converted at process block 128 into a format such as DICOM-RT which is a standard that can be exported to commercially available medical systems over the intranet.

The treatment zone image may be exported and used in a number of different systems. One such system is a radiation therapy planning system, which is a workstation that enables images to be imported and used to plan further treatment. In such case, the imported treatment zone image is registered with another, anatomic image which is also imported into the therapy planning system. The fiducials that appear in both images are used to register them and the result is an anatomic image of the patient with the treatment zone superimposed over it. The transparency of the treatment zone image can be changed to see the underlying anatomy. It can then be used as a target structure, or an object of avoidance structure, for radiation therapy planning. Prior to or after exportation the thickness of the 3D treatment zone image can be increased, symmetrically in each direction beyond the image, for better viewing within CT images. Or, additional thickness can be added in one direction from the 3D treatment zone image. As an example, a surgeon might create an image on the surface of an anatomic structure or tissue where she is concerned about her ability to fully resect, where she is concerned about the presence of microscopic residual disease, or where frozen section analysis reveals the presence of residual disease that cannot be resected. In this situation, thickness can be added deep to the drawing to represent the suspected degree of invasion into the anatomic structure or tissue.

The treatment zone image may also be imported by a radiation emitting system to assist in administering radiation to the patient. Such treatment systems may be used intra-operatively or post-operatively. A radiation therapy system generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the patient. An example of a plate arrangement is a set of four plates that can be used to define an opening for the radiation beam. Alternatively, a beam shielding device can include multiple leaves (commonly called "multileaves"), for example, a plurality of relatively thin plates or rods, typically arranged as opposing leaf pairs. The plates themselves are formed of a relatively dense and radiation impervious material and are generally independently positionable to delimit the radiation beam. Alternatively, in systems which employ electron beams the electron beams are usually shaped via the placement of cylindrical electron cones, circular or elliptical, mounted in the treatment head. The size of the electron-treated area is controlled via selection of an electron cone of desired diameter.

The beam shielding device defines a field on the object to which a prescribed amount of radiation is to be delivered. The usual treatment field shape results in a three-dimensional treatment volume which includes segments of normal tissue, thereby limiting the dose that can be given to a tumor located at the isocenter. Avoidance of delivery of radiation to the organs surrounding and overlying the tumor determines the dosage that can be delivered to the tumor.

Intra-operative linear accelerator-based radiation therapy generally involves the administration of electrons via a single direct, en face field. A key advantage of delivering radiation therapy intra-operatively is the ability of the surgeon to move structures that are radiosensitive out of the direct path of the electrons and apply a heavier dose to the target tissues. Often, therefore, the surface of the anatomic structure or tissue felt to be at high risk for harboring gross or microscopic residual cancer after gross total or partial resection is exposed directly to the electron beam. Based on the thickness of the residual cancer, and the likely depth of invasion of residual gross or microscopic cancer deep to the surface of the visualized organ or tissue at risk, an electron energy is chosen that will deliver sufficient dose to the area at risk, with rapid dose fall-off deep to the area at risk. Based on the diameter of the imaged 3D treatment zone, an electron cone of optimal diameter for coverage of the treatment zone with minimization of dose delivered to surrounding structures, is chosen and mounted to the treatment head. The linear accelerator is moved into proper position to deliver an electron beam to the 3D treatment zone. To take maximum advantage of the dose distribution properties of electrons, an attempt is made to place the electron cone in position perpendicular to the surface of the exposed organ or tissue at risk. The patient is then irradiated.

The 3D treatment zone image is used to help aim the electron beam. The treatment system includes an alignment apparatus such as that described in the above-cited published US patent application which aligns the treatment system with the patient. This is done using the implanted fiducials. As a result, the electron cone produced by the treatment system is registered with the patient. The imported treatment zone image is also aligned with the patient using the patient reference points in the image and the fiducials implanted in the patient. As a result, the treatment zone image can be registered with an image of the electron cone produced on a display located near the surgeon and radiation oncologist. The linear accelerator is brought into proper position such that the 3D treatment zone depicted on the display is aligned within the displayed border of the electron cone. The electron cone is positioned to abut the surface of the organ or tissue to be treated and the angle of the gantry, along with the position of the linear accelerator relative to the patient is adjusted as necessary. When the surgeon and radiation oncologist are satisfied that the displayed electron cone is aligned with the displayed 3D treatment zone, the desired dose is delivered. The 3D treatment zone image thus serves as a target on the display at which the liner acceleration may be aimed.

The treatment zone image may also be used in a post-operative radiation therapy system. The post-operative delivery of radiation by a radiation therapy device is prescribed and approved by a radiation oncologist. The prescription is a definition of, for example, a particular volume and the level of radiation permitted to be delivered to that volume, from each of usually multiple treatment fields. The present invention enables this prescription to be more accurately defined by providing a three-dimensional treatment zone image that is registered with reference points in the patient, and that can be registered with the radiation beam produced by the therapy device. Actual operation of the radiation equipment is normally done by a therapist. When the therapist administers the actual delivery of the radiation treatment as prescribed by the radiation oncologist, the radiation-emitting device is programmed to deliver that specific treatment.

Figure 4:
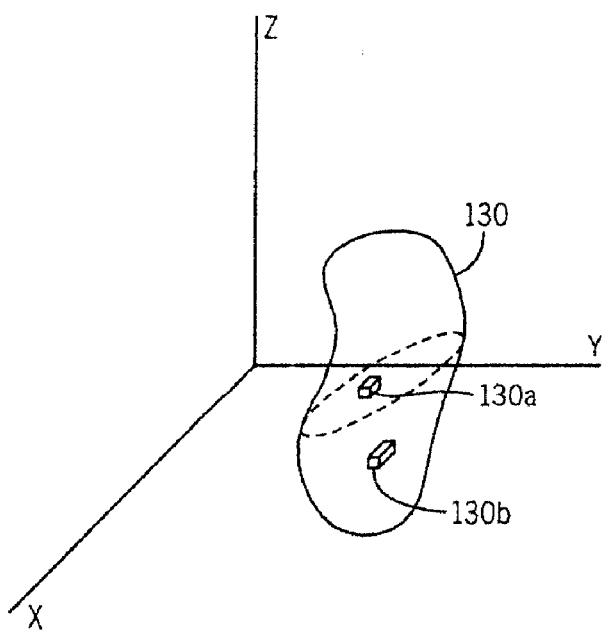
FIG. 4 is a pictorial representation of a treatment zone.

Referring to FIG. 4, a three dimensional treatment zone image is shown. The amount of radiation to be delivered to the volume 130 is not uniform throughout the volume, however. Typically, the amount of radiation to be delivered is highest in the center and decreases outwardly, though not necessarily uniformly. Thus, for example, voxels 130*a* and 130*b* could receive different levels of radiation. As can be appreciated, the goal of radiation therapy is to deliver as close a dosage as possible to the prescribed dosage requirements at each of the voxels 130*a*, 130*b* etc. The goal of treatment optimization is to determine the best way to achieve this treatment fitting. Treatment fitting is accomplished by applying radiation at a series of different gantry angles. The leaves of a multi-leaf collimator and/or other shielding device(s) delimit the radiation beam at particular angles and thus define the radiation field for the particular gantry angle.

Figure 5:
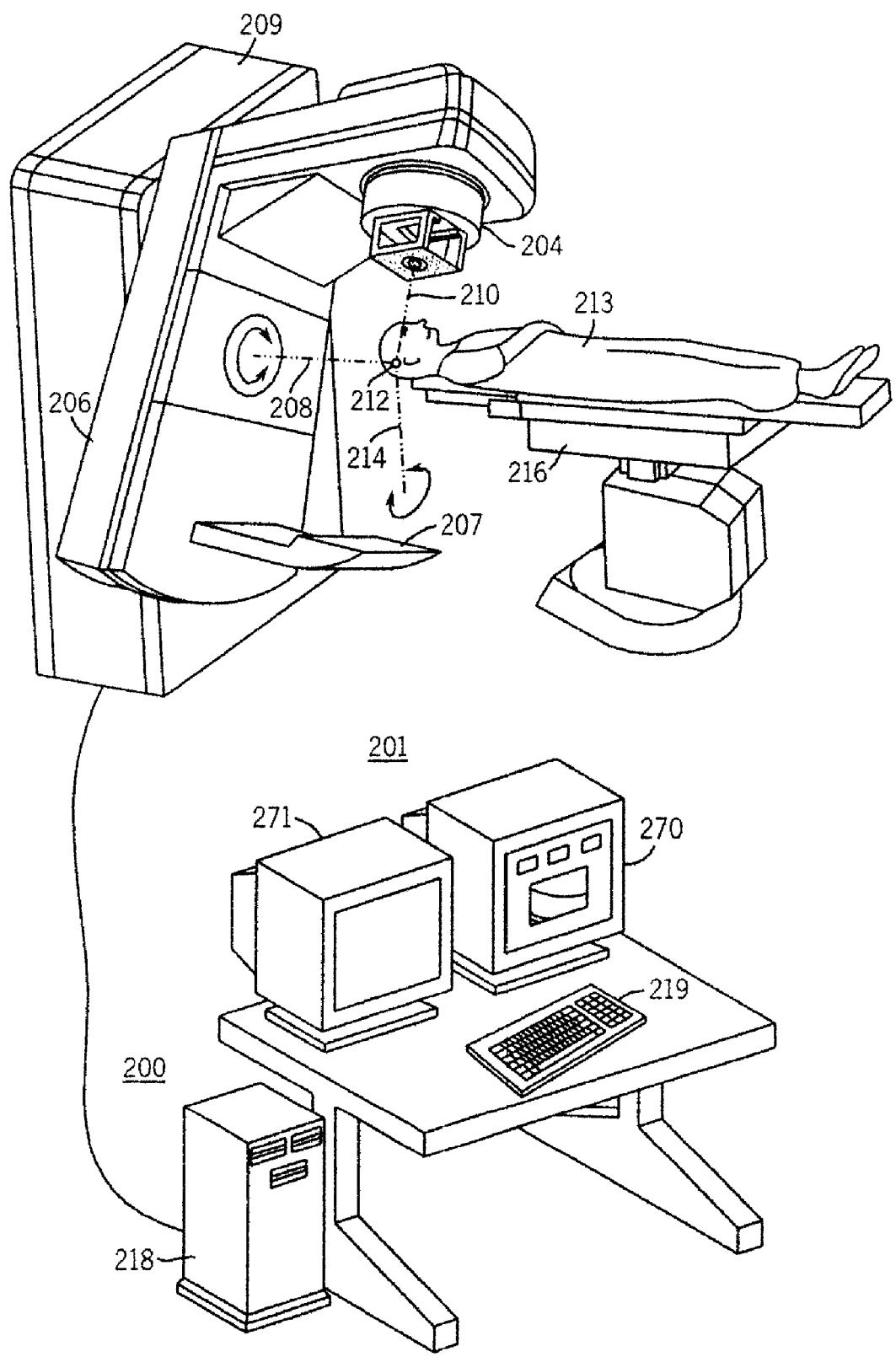
FIG. 5 is a pictorial representation of a radiation treatment system to which three-dimensional treatment zone images produced on the workstation of FIG. 1 may be exported.

Turning now to FIG. 5, a radiation treatment system is shown and generally identified by reference numeral 201. The radiation treatment apparatus 201 is representative of, for example, the Mevatron™ series of machines available from Siemens Medical Systems, Inc. The radiation treatment system 201 includes a beam shielding device (not shown) within a treatment head 204, a control unit (not shown) in a housing 209 and a treatment unit 200. The radiation treatment apparatus 201 includes a gantry 206 which can be swiveled around a horizontal axis of rotation 208 in the course of a therapeutic treatment. The treatment head 204 is fastened to projection of the gantry 206. A linear accelerator is located in the gantry 206 to generate the high powered radiation required for the therapy. The axis of the radiation bundle emitted from the linear accelerator and the gantry 206 is designated by 210. Electron, photon or any other detectable radiation can be used for the therapy. In the post-operative setting, photons are almost always used.

During the treatment, the radiation beam is trained on a treatment zone 212 of a patient 213 who is to be treated and who lies at the isocenter of the gantry rotation. The rotational axis 208 of the gantry 206, the rotational axis 214 of a treatment table 216, and the beam axis 210 intersect at the isocenter.

The radiation treatment system 201 also includes a central treatment processing or control unit 200 which is typically located apart from the radiation treatment apparatus 201. The treatment unit 200 may be a Windows NT workstation, for example. The radiation treatment apparatus 201 is normally located in a different room to protect the therapist from radiation. The treatment unit 200 includes output devices such as at least one visual display unit or monitor 270 and an input device such as a keyboard 219 or other input devices such as a mouse or trackball (not shown). Data can be input also through data carriers such as data storage devices or through an institutional Intranet connection. By using the keyboard 219 or other input device, the therapist enters into the treatment unit 200 the data that defines the radiation to be delivered to the patient. On the screen of a monitor 71 various data can be displayed before and during the treatment as will be described below.

As shown in FIG. 5, the treatment apparatus 201 has an array of x-ray detectors 207 supported by the gantry 206 and positioned opposite the treatment head 4. An image of the treatment zone can be acquired and displayed on the monitor 271 by emitting a radiation beam from the treatment head 204 at a low level and detecting the attenuation of the radiation beam that passes through the patient 213 to the detectors 207.

The gantry 206 is rotated to acquire attenuation measurements at a series of view angles, and from these measurements a three-dimensional image of the region around the system isocenter is reconstructed. As will be described in more detail below, this limited imaging capability is employed to produce an image of the patient that is aligned with the treatment system isocenter. Or stated another way, this image depicts the patient anatomy that is the target of the treatment system. The field of view of this image is large enough to see anatomical landmarks or implanted fiducials that surround the target tissues. For a more detailed description of the structure and operation of the treatment apparatus 201 and treatment unit 200, reference is made to U.S. Pat. No. 6,222,544 entitled "Graphical User Interface For Radiation Therapy Treatment Apparatus" which is incorporated herein by reference.

Figure 6:
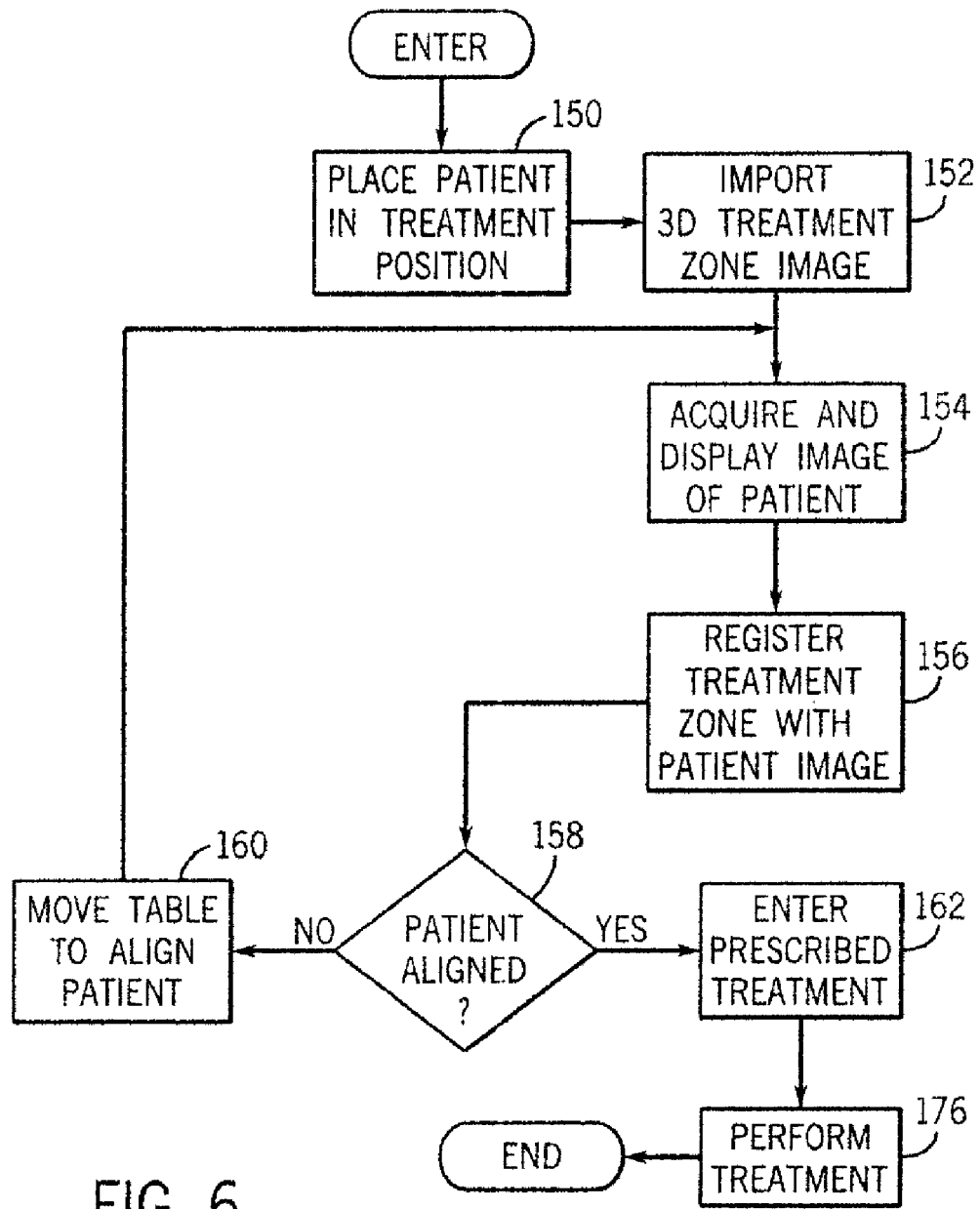
FIG. 6 is a flow chart which describes the operation of the radiation treatment system of FIG. 5.

Referring to FIG. 6, the first step in treating a patient according to the present invention is to place the patient on the table 216 as indicated at process block 150 and position the patient such that the tumor to be radiated is at the system isocenter. Precise alignment is not likely at this time, but at least the tumor should be in the field of view of the image to be acquired with the treatment system 201.

As indicated by process block 152, the 3D treatment zone image is then imported over the Intranet along with any other treatment prescription data from the oncologist. As indicated at process block 154, a scan is then performed with the treatment apparatus to acquire an image of the patient. This image will depict the treatment zone and surrounding tissues as well as any anatomic landmarks that were identified or fiducials that were implanted in the patient. The next step is to register the imported treatment zone image with the patient image as indicated at process block 156. This can be done manually by right clicking and moving the 3D treatment zone image until the three or more reference points therein are aligned with the anatomical landmarks or implanted fiducials depicted in the patient image. This registration step may also be done automatically using programs such as that described in U.S. Pat. No. 6,408,107 entitled "Rapid Convolution Based Large Deformation Image Matching Via Landmark And Volume Imagery", which is incorporated herein by reference.

Figure 7:
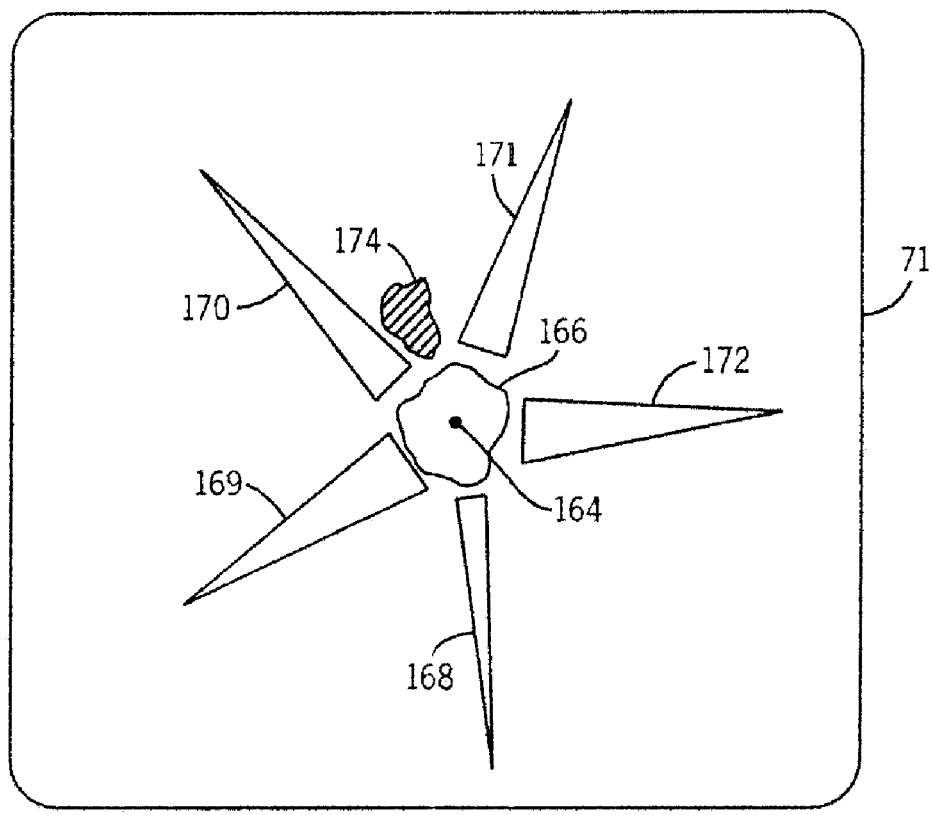
FIG. 7 is a display which is produced by the radiation treatment system of FIG. 5 to assist in planning the treatment process.

As indicated at decision block 158, a determination can then be made if the desired treatment zone is properly aligned at the system isocenter. If not, the patient table 216 is moved an appropriate amount in the proper direction to achieve alignment as indicated at process block 160. The system then loops back to acquire another patient image and register it with the treatment zone image to determine if the patient is properly aligned. This process can be repeated as many times as necessary to achieve proper alignment. As shown in FIG. 7, proper alignment is achieved when the system isocenter indicated at 164 on display 271 is centered in the treatment zone image indicated at 166.

As indicated at process block 162 the prescribed treatment information is then entered into the treatment unit 200. As discussed above, the radiation treatment is comprised of a series of exposures to a radiation field of prescribed strength, duration, gantry angle and field size. As shown in FIG. 7, as each treatment exposure is entered a corresponding icon 168-172 is produced on the display 271 to show the radiation field that will be produced relative to the treatment zone image 166. These treatment exposures can be easily edited to insure that all portions of the treatment region receive their prescribed dose. Also, if any high risk tissues were identified by the surgeon, these will also appear in the imported image and be displayed as indicated by the region 174. In planning the series of treatment exposures, it is relatively easy to select gantry angles and field sizes that will avoid exposing this region 174.

It should be apparent that many variations are possible from the preferred embodiments described herein without departing from the spirit of the invention. The 3D treatment zone image may be employed with many different treatment planning and treatment delivery systems, some of them used intra-operative and some of them used post-operative. In any case, the maximum clinical value is achieved when the treatment zone image and the patient are registered with each other, with the images used for treatment planning, and with the coordinate system of the treatment device such that the treatment zone image can serve as an accurate target for treatment planning and delivery.

It should also be apparent that the present invention may also be employed with systems that register the tracking system with pre-operatively obtained images of the patient. In such systems instrument 3 is visible on display 12 intra-operatively within or relative to the pre-operative images. Examples of such systems include the VectorVision® navigation system manufactured by BrainLAB, used for brain tumor resections, along with an intrabody navigation system that uses electromagnetic radiation to track the position of a bronchoscope relative to pre-operative images, described in U.S. Pat. No. 6,593,884 (entitled "Intrabody navigation system for medical applications"). Referring to FIG. 1, in the preferred embodiment the pre-operative image is imported to the workstation 7 and presented on CRT display 12. The tracking system is registered with this image by placing the tip of instrument 3 at different landmark locations on the patient 1 and moving the displayed image until the same anatomical landmarks therein are aligned with the tracking system landmarks also displayed on the CRT 12. In this embodiment, 3D treatment zones are drawn with the tip of the instrument 3 as described above and the resulting 3D treatment zone is visualized on display 12 with the imported image as it is being created. The registered pre-operative images in this alternative embodiment serve as the patient reference points and are stored as part of the treatment zone image. In this embodiment, the use of fiducials or anatomic landmarks for registration, is optional but not necessary.

In most cases the registration of the treatment zone image will be accomplished in the subsequent treatment system by registering the accompanying anatomical "patient reference points" image with an image acquired using an imaging system that is integral with the treatment system as described above. See also U.S. Pat. Nos. 5,418,827 and 5,661,773 which disclose the use of a CT system to perform the imaging function where better quality images of the patient are acquired. Such registration of the two anatomical images can be performed automatically using commercially available image registration software.

It is also possible to register, or align, the imported treatment zone image without the need for acquiring an image of the patient. For example, fiducials that passively emit radio frequency signals (each fiducial with a unique signal) may be implanted in the patient. The 3D treatment zone images may be created and registered relative to the RF fiducials, using methods described above. An RF tracking system such as that described in the above-cited US patent application can be used to locate the positions of the RF fiducials relative to the treatment system isocenter. The 3D treatment zone image can then be aligned with these locations using the patient reference points therein.

The 3D treatment zone workstation can be used exclusively for generating, registering, viewing, and exporting 3D treatment zones. Alternatively, it can exist as part of a system used for multiple cancer-related intra-operative functions. Ultrasound can be integrated with the cart containing the workstation, for intra-operative imaging. When the ultrasound probe is optically tracked, ultrasound can be used for 3D localization of the fiducials to which the 3D treatment zone is registered. In addition, however, ultrasound can also be used to identify existing structures intra-operatively for surgical management, but also for later radiation therapy or other targeting. As an example, liver metastases are often best imaged via intra-operative ultrasound. If a metastasis is identified but not resected, radio-opaque fiducials (or RF transponders) can be implanted near the metastasis. The ultrasound image of the tumor can be registered to the fiducials. When the fiducials are identified later in the anatomic images imported to a radiation therapy treatment planning system, the ultrasound image of the metastasis can be viewed in the images relative to the fiducials, and then targeted. Similarly, when fiducials are radiopaque and identified with an x-ray or fluoroscopy-based radiation therapy tracking system (used for producing static images or for real-time images used for tracking or gating), the ultrasound image of the metastasis can be viewed and tracked relative to the fiducials and field borders. When fiducials are localized in three-dimensional space via an RF-based localization system, the intra-operative ultrasound images can be similarly viewed, tracked, and targeted.

The workstation used for 3D treatment zone generation can also be integrated with an intra-operative soft tissue guidance system that tracks target location, orientation, and shape relative to fiducials, and relative to surgical instruments. During surgery, radiation therapy, or other procedures, the fiducials to which 3D treatment zones, ultrasound images, or other images are registered can change in orientation or position relative to the other fiducials. At the time of registration, the position of each point used to generate the 3D treatment zone is therefore calculated, relative to each fiducial. As the relative positions of the fiducials change, the points of the 3D treatment zone are repositioned by software which calculates the most likely positions of the points, based on the new fiducial positions. The outer border of the image is then "morphed" so that its outer surface continues to pass through the points. The positions of representative points forming the outer surfaces of other tumor images, such as ultrasound images, can be calculated relative to the fiducials, so that these images can be similarly morphed as the fiducials change in relative position and orientation. Similarly, the outer borders of physiologic images such as PET or MRI or SPECT images of tumors can be imported relative to the fiducials, and similarly morphed as the fiducials change in relative position and orientation. Finally, once the borders of physiologic tumor images have been registered to fiducials, internal points or individual voxels of physiologic tumor images can be registered to fiducials. The internal anatomy can be similarly morphed as the fiducials change in relative position and orientation. As described in co-pending US patent application filed herewith and entitled "Dynamic Tumor Diagnostic And Treatment System Employing Isonumeric Contours" the internal physiology of tumors can be displayed isonumerically, such that voxels internal to the borders of a tumor image that are of equal or similar intensity are connected by three-dimensional contour lines. These contours, representing the isophysiologic areas within a tumor similar to the way elevation contours represent areas of equal elevation on a topographic map, demonstrate physiologic gradients and other forms of physiologic heterogeneity within tumors. These internal isonumeric contours can be similarly morphed as the fiducials change in relative position and orientation.

Using this system, physiologic images can be used for real time targeting of radiation therapy. However, they can also be used for surgical targeting, with the outer borders or internal contours serving as dissection planes. If desired, a selected amount of surgical margin can be added to any border or contour, and similarly morphed as the tissue is surgically manipulated. These images can also be merged with ultrasound or other images, all of which are registered to the fiducials, to form composite images, still registered to the fiducials.

I claim:

1. A method for planning the treatment of a region in a patient, the steps comprising:
   a) producing a treatment zone image by
      i) moving an instrument over a portion of a patient to establish a set of patient reference points using a tracking system that records the location of an instrument; and
      ii) moving the instrument over a portion of the patient to mark a set of treatment zone boundary points using the instrument, wherein the boundary points define a three-dimensional region in the patient that is to receive treatment;
   b) aligning the patient in a treatment system;
   c) registering the treatment zone image with the patient using the set of patient reference points; and
   d) displaying the registered treatment zone image to indicate where in the patient the treatment is to be directed.

2. The method as recited in claim 1 in which the set of patient reference points are established by implanting a set of fiducials around said region and recording their locations with the instrument.

3. The method as recited in claim 1 in which step c) includes acquiring an image of the patient which depicts the patient reference points, and aligning the patient reference points in the treatment zone image with the patient reference points depicted in the patient image.

4. The method as recited in claim 3 in which a patient reference point corresponds with an anatomical landmark depicted in the patient image, and the treatment zone image includes data that relates a patient reference point therein to an anatomical landmark.

5. The method as recited in claim 3 in which a patient reference point corresponds with an implanted fiducial depicted in the patient image.

6. The method as recited in claim 2 in which step c) includes determining the locations of fiducials implanted in the patient and aligning the patient reference points in the treatment zone image with these locations.

7. The method as recited in claim 1 in which step a) includes marking a second set of boundary points that define a second three-dimensional region in the patient.

8. The method as recited in claim 1 in which the step of moving the instrument over a portion of the patient to mark a set of treatment zone boundary points includes marking a three-dimensional contour of a portion of the patient including the treatment zone.

9. A system for producing a treatment zone image indicative of a region in a patient to receive treatment, which comprises:
   an instrument configured to be moved about the region in the patient to mark locations in the patient;
   a tracking system for recording locations marked by the instrument;
   means for storing patient reference points;
   means for storing as a plurality of boundary points a plurality of locations marked by the instrument which define a region of tissues in the patient for treatment; and
   means for producing a treatment zone image which depicts the region of tissues to be treated and the patient reference points.

10. The system as recited in claim 9 in which the tracking system is an optical tracking system.

11. The system as recited in claim 9 which further includes: means for storing as a plurality of boundary points a plurality of locations marked by the instrument which define a second region of tissues in the patient, and the means for producing a treatment zone image produces a treatment zone image which also depicts the second region of tissues.

12. The system as recited in claim 9 in which the means for producing a treatment zone image includes means for producing a three-dimensional image of a surface that passes through said plurality of boundary points.

13. The system as recited in claim 9 in which the means for storing patient reference points includes means for designating a plurality of locations marked by the instrument as the patient reference points.

14. The system as recited in claim 9 in which the means for storing patient reference points includes means for importing an image of the patient, means for registering the imported image with the tracking system, and means for storing the registered image as the patient reference points.

15. The system as recited in claim 9 in which the tracking system is configured to monitor the instrument to determine a three-dimensional contour of the region of tissues to be treated.

* * * * *